United States Patent [19]

Eibl

[11] Patent Number: 4,739,095

[45] Date of Patent: Apr. 19, 1988

[54] DERIVATIVES OF N,N-(2-CHLORO-ETHYL)-PHOSPHORIC ACID AMIDE

[75] Inventor: Hansjörg Eibl, Bovenden, Fed. Rep. of Germany

[73] Assignee: Max-Planck-Gesellschaft zur Förderung der Wissenschaften E.V., Göttingen, Fed. Rep. of Germany

[21] Appl. No.: 869,831

[22] Filed: Apr. 30, 1986

Related U.S. Application Data

[63] Continuation of Ser. No. 598,287, filed as PCT DE83/00122, Jul 6, 1983, published as WO84/00368, Feb. 2, 1984, abandoned.

[30] Foreign Application Priority Data

Jul. 6, 1982 [DE] Fed. Rep. of Germany ....... 3225227

[51] Int. Cl.$^4$ ............................................... C07F 9/24
[52] U.S. Cl. .................................. 558/185; 558/199; 260/403
[58] Field of Search ................. 558/185, 199; 260/403

[56] References Cited

U.S. PATENT DOCUMENTS 3,035,080  5/1962  Arnold et al. .................... 260/950

FOREIGN PATENT DOCUMENTS 8400368  2/1984  World Int. Prop. O. .......... 558/185

OTHER PUBLICATIONS

Arnold et al, "Angewante Chemie", Bard 70, Nr 17/18, Sep. 23, 1958, pp. 539-544.

Kosolapoff, "Organophosphorus Compounds"(1955), pp. 279-288.

Primary Examiner—Anton H. Sutto
Attorney, Agent, or Firm—Felfe & Lynch

[57] ABSTRACT

The invention concerns derivatives of N,N-bis(2-chloroethyl)-phosphoric acid amide of general formula I

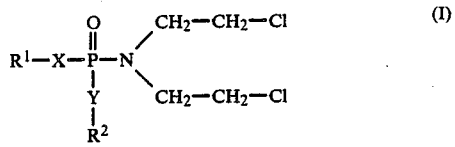

wherein X and Y are the same or different and signify oxygen or $NR^3$, $R^1$ and $R^2$ are the same or different and $R^1$ signifies the radical $CH_2(OR^4)—CH_2—CH_2—$, $CH_2(OR^4)—CH(CH_3)—CH_2—$ or $CH_2(OR^4)—CH(OR^5)—CH_2—$ and, when X is an $NR^3$ group, can also be hydrogen, $R^2$ possesses one of the meanings of $R^1$ or is ethyl, propyl, allyl, propenyl, chloroethyl, methyl or benzyl, $R^3$ is hydrogen, methyl, ethyl, propyl or allyl and wherein the radicals $R^4$ and $R^5$ are the same or different and represent an alkyl radical R or an acyl radical —COR, whereby R signifies a straight-chained or branched, saturated or unsaturated alkyl group with 1 to 25 carbon atoms, or an aralkyl radical with 1 to 25 carbon atoms in the alkyl chain, and one of the radicals can also be a hydrogen atom, as well as processes for their preparation. The compounds according to the invention display an outstanding antitumour action comparable with the action of cyclophosphamide.

4 Claims, No Drawings

DERIVATIVES OF N,N-(2-CHLORO-ETHYL)-PHOSPHORIC ACID AMIDE

This application is a continuation of application Ser. No. 598,287, filed as PCT DE83/00122 Jul. 6, 1983 published as WO84/00368, Feb. 2, 1984, now abandoned.

The invention concerns new derivatives of N,N-bis-(2-chloroethyl)-phosphoric acid amide which, in particular, possess an outstanding anti-tumour action.

Cyclophosphamide is a proven cytostatic which is commercially available under various designations. The cancerotoxic selectivity of N-2-chloroethylamidooxazaphosphorines, such as cyclophosphamide (H. Arnold and F. Bourseaux, Angew. Chem., 70 (1958), 539) is closely bound up with the special ring structure of the oxazaphosphorine ring with a propanolaminephosphoric acid ester grouping. The principle of a transport active form is here present. The transport form of cyclophosphamide is inactive and its activation must take place in the liver. The active form of cyclophosphamide is assumed to be the phosphoric acid diamide of the formula

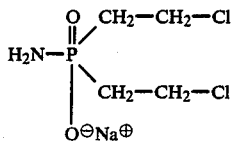

It is the object of the present invention to avoid the activation in the liver and to utilise general activation principles, such as, for example, small pH differences between normal and tumour cells. This problem is solved by the present invention The object of the invention are derivatives of N,N-bis-(2-chloroethyl)-phosphoric acid amide of the general formula I

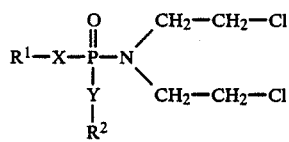

wherein X and Y are the same or different and signify O or $NR^3$, $R^1$ and $R^2$ are the same or different and $R^1$ signifies the radical $CH_2(OR^4)-CH_2-CH_2-$, $CH_2(OR^4)-CH(CH_3)-CH_2-$ and especially the radical $CH_2(OR^4)-CH(OR^5)-CH_2-$, and, when X is an $NR^3$ group, can also be hydrogen, $R^2$ possesses one of the meanings of $R^1$ and is preferably ethyl, propyl, allyl, propenyl, chloroethyl and especially benzyl and, in the first place, methyl, $R^3$ is hydrogen, methyl, ethyl, propyl or allyl and wherein the radicals $R^4$ and $R^5$ are the same or different and represent an alkyl radical R or an acyl radical $-COR$, whereby R signifies a straight-chained or branched, saturated or unsaturated alkyl group with 1 to 25 carbon atoms, or an aralkyl radical with 1 to 25 carbon atoms in the alkyl chain, and one of the radicals can also be a hydrogen atom.

An alkyl radical R can be branched or, preferably, unbranched. As alkyl radical, R can also be substituted and possesses in one of the radicals $R^4$ or $R^5$ preferably 1 to 7, especially 1 to 3 carbon atoms, and in the other radical $R^4$ or $R^5$ 16 to 20 carbon atoms. A substituted alkyl radical R is preferably only contained in one of the radicals $R^4$ or $R^5$. Substituents in the alkyl radical R are, for example, hydroxyl, halogen, mesyloxy, alkoxy, alkenyloxy, or alkynyloxy with 3 to 12 carbon atoms or dihydroxypropyloxy.

An acyl group $-COR$ is derived especially from a natural fatty acid, such as, for example, behenic, lauric, stearic, palmitic, myristic, capric or arachidic acid.

In an aralkyl group R, the aryl radical is preferably a phenyl radical possibly substituted by alkyl with 1 to 7, especially 1 or 2 carbon atoms and the alkyl group preferably possesses 1 to 4 carbon atoms. It is, for example, phenethyl and especially benzyl.

The radicals $R^4$ and $R^5$ differing from one another can also only differ in their steric configuration or only be the content of different isotopes, such as, for example, deuterium, tritium, $C_{14}$; the glyceride radicals, especially the radical $-CH_2(OR^4)-CH(OR^5)-CH_2-$, are preferably derived from the pure stereoisomeric D- or L-forms, especially from the biologically-active stereoisomeric forms.

A glyceride radical $R^1$ or $R^2$ is derived, for example, from the glycerol derivatives of the formula I of German Patent Application No. P 31 30 867 and especially from the ether lecithines of formula I of published German Patent Application No. 26 19 686, from the glycerol derivatives of the formulae II, III or IV of the German Patent Application of the same Applicant "New D-mannitol derivatives as starting products for the synthesis of phospholipids" of the same application date, whereby the radicals $R^1$ and $R^2$ in these Applications correspond to the radicals $R^4$ and $R^5$ in the glyceride radical.

Especially preferred is the compound of formula I, in which $R^1$ signifies 3-octadecyloxy-2-methoxypropyl, $R^2$ methyl, X the NH group and Y oxygen.

It has been found that the compounds of the general formula I according to the invention possess a very good antitumour effectiveness which is comparable with that of cyclophosphamides and, because of the low toxicity, in some cases are superior to these. On the basis of their structure, the compounds according to the invention possess a high selectivity against tumour cells, with a clearly lower damaging action on healthy cells.

In the compounds of formula I according to the invention, the active form is present in a neutral membrane-like transport form by coupling on to a lipid molecule. Because of their hydrophobic groups, they are easily incorporated into the cell membrane. In the weakly acidic range, such as is present in tumour cells, a splitting then takes place with the liberation of the cytostatically-effective polar active form. The cell membranes of tumour cells are thereby preferably attacked, whereas the membranes of normal cells remain relatively unaffected.

On the basis of their structure, it is possible to control the lipophilia or hydrophilia of the compounds of formula I according to the invention and to adapt them to special problems. By means of a simple variation of the structure (especially in the meaning of the radicals $R^1$ and/or $R^2$), the conversion from the transport form into the active form can, furthermore, be speeded up or slowed down, as desired.

The subject of the invention is also a process for the preparation of the compounds of general formula I, which is characterised in that one (1) reacts N,N-bis-(2-chloroethyl)-amidophosphoric acid dichloride (a) with a compound $R^1$—XH and the reaction product obtained then with a compound of the formula $R^2$—YH, or (b) with a compound of the formula $R^2$—YH and the reaction product obtained then with a compound of the formula $R^1$—XH, whereby $R^1$ $R^2$, X and Y possess the above-given meaning, or (2) reacts phosphorus oxychloride with $R^1$—XH, reacts the $R^1$X—POCl$_2$ obtained with bis-(2-chloroethyl)amine and the compound obtained then with $R^2$—YH, whereby $R^1$, $R^2$, X and Y possess the above-given meaning.

The individual reaction steps of the process variants (1) and (2) can take place under the conditions known for such reactions. The reaction of $R^1$X—POCl$_2$ with bis-(2-chloroethyl)-amine takes place in the presence of a base, such as preferably triethylamine, in an inert organic solvent, such as for example in dioxan, chloroform, carbon tetrachloride, methylene chloride or preferably in tetrahydrofuran. For example, the compound $R^1$—XH (0.1 mol) is dissolved in 100 ml. tetrahydrofuran and added dropwise at 0° C. to POCl$_3$ (0.15 mol) which contains triethylamine (0.12 mol). One slowly warms up to 20° C., filters off from precipitated triethylamine hydrochloride and mixes dropwise at 20° C. with bis-(2-chloroethyl)amine (0.1 mol) in 100 ml. tetrahydrofuran which contains triethylamine (0.15 to 0.2 mol). The reaction product obtained is then reacted with $R^2$—YH, for example with a) (for Y=O) methanol, ethanol or allyl alcohol, or b) (for Y=NR$^3$) with ammonia, methylamine or dimethylamine.

The starting compounds for the process according to the invention are known or can be prepared according to per se known methods. Preferred synthesis possibilities for the compounds $R^1$—XH or $R^2$—YH, in which $R^1$ and $R^2$ signify a glyceride radical, are described, for example, in German Patent Application No. P 31 30 867 of the same Applicant of Aug. 4, 1981, or in the German Patent Application of the same Applicant and with the same Application date "New D-mannitol derivatives as starting products for the synthesis of phospholipids", or in published German Patent Application No. 26 19 686.

The subject of the Application are also medicaments which contain one or more compounds of the formula I as active materials. Besides the usual pharmaceutical confectioning and/or dilution agents, these medicaments can contain, besides the compounds of formula I, possibly also still further active materials for the support of the therapy insofar as these, together with the compounds of formula I according to the invention, do not display any undesired side effects.

The effectiveness of compounds of general formula I on the growth of tumours is expediently demonstrated on tumours in experimental animals. For this purpose, various experimental tumours are used, for example the Ehrlich ascites tumour, a methylcholanthrene-induced tumour and a myeloma tumour in mice, furthermore a chemical-induced rat tumour. The antitumour substances are administered parenterally into the tumour-carrying experimental animals. The intravenous and the intra- or subcutaneous administration is preferred. The orally administerability is, in the case of correspondingly higher dosage of the antitumour agent, also not excluded in the case of a physiologically acceptable composition, for example in capsules.

As dosage, in the case of parenteral administration, it has proved expedient to use about 0.05 to 5 mg./kg. of body weight. In order to allow the antitumour agent to persist for a comparatively long time in circulation, it is frequently desirable to administer the agents daily or at two or three day intervals.

The following Examples further explain the invention, without limiting it thereto.

EXAMPLES

Preparation of Amines Which Contain the Radical R$_1$

In the following is described the preparation of new amines which possess a glycerol fundamental substance or an alkanediol-($\omega$, $\omega'$) fundamental substance ($R^1$=CH$_2$(OR$^4$)—CH$_2$—CH$_2$—, CH$_2$(OR$^4$)—CH(CH$_2$)—CH$_2$— or CH$_2$(OR$^4$)—CH(OR$^5$)—CH$_2$—). Starting products are the corresponding diethers or monoethers, for example 1-octadecyl-2-methyl-sn-glycerol. The alcohol group of the diether is first mesylated and then reacted with excess ammonia.

Mesylation

The alcohol (0.1 mol) is dissolved in 300 ml. THF and mixed with triethylamine (0.2 mol). Mesyl chloride (0.1 mol) is added dropwise at 10° C., with stirring, until the starting product can no longer be detected. After the addition of 300 ml. diisopropyl ether, it is washed with 300 ml. water, the ether phase dried over Na$_2$SO$_4$ and the solvent removed in a vacuum. The oil remaining behind is further reacted directly.

Amination

The oily residue from the mesylation (0.1 mol) is heated to 50° C. in 100 ml. chloroform, 300 ml. DMF, 200 ml. methanol and 200 ml. 25% ammonia (in water: 3 mol) until the starting product has completely reacted. One extracts with chloroform, removes the solvent and purifies small amounts by chromatography. The main amount is used directly for the further reactions. The yields lie at 90%, referred to the starting alcohol.

The following compounds were prepared in this way:

1-octadecyl-2-methyl-3-desoxy-3-amino-sn-glycerol (C$_{22}$H$_{47}$NO$_2$; 357.626): calc.: C, 73.89; H, 13.25. found: C, 74.01; H, 13.34.

1-octadecyl-2-pentyl-3-desoxy-3-amino-sn-glycerol (C$_{26}$H$_{55}$NO$_2$; 413.73): calc.: C, 75.48; H, 13.40. found: C, 75.61; H, 13.63.

1-octadecyl-2-dodecyl-3-desoxy-3-amino-sn-glycerol (C$_{33}$H$_{69}$NO$_2$; 511.92): calc.: C, 77.43; H, 13.59. found: C, 77.71; H, 13.67.

1. Preparation of the Phosphoric Acid Diamide Monochlorides (A) N,N-bis-(2-chloroethyl)-amidophosphoric Acid Dichloride:

Phosphorous oxychloride (0.15 mol) in 100 ml. THF are mixed dropwise at 10° C. with bis-chloroethylamine (0.1 mol) in 100 ml. THF and triethylamine (0.15 mol). After ending of the reaction (TLC verification), triethylamine hydrochloride is filtered off and the filtrate, after the addition of 50 ml. toluene, evaporated. The oily residue is immediately further reacted.

(B) N,N-bis-(2-chloroethyl)-amido-N'-alkylamidophosophoric Acid Monochloride

The oily residue (0.1 mol) from A) is taken up in 100 ml. THF and mixed dropwise at 10° C. with alkylamine (0.1 mol) in 100 ml. THF and triethylamine (0.2 mol). After ending of the reaction (TLC verification), it is filtered off from triethylamine hydrochloride and the filtrate further reacted directly (see 2, A and B).

2. Alcoholysis or Amidolysis of the Phosphoric Acid Diamide Monochlorides (A) Alcoholysis:
N,N-bis-(2-chloroethyl)-amido-N'-alkylamidophosphoric Acid Alkyl Ester (Transport Form)

The solution in THF (B; 0.1 mol) is reacted with a primary alcohol (1 mol). After ending of the reaction (TLC verification), it is mixed with 200 ml. chloroform and washed twice with 200 ml. water. The solvent is stripped off and the residue chromatographed on silica gel. The yield lies at 90%.

The following compounds were prepared in this way:

N,N-bis-(2-chloroethyl)-amido-N'-octadecylamidophosphoric acid methyl ester ($C_{23}H_{49}Cl_2N_2O_2P$; 487.55): calc.: C, 56.55; H, 10.13; N, 5.75; P, 6.35. found: C, 56.91; H, 10.24; N, 5.86; P, 6.31.

N,N-bis-(2-chloroethyl)-amido-N'-(1-octadecyl-2-methyl-3-desoxy-sn-glycerol)-3-amidophosphoric acid methyl ester ($C_{27}H_{57}Cl_2N_2O_4P$; 575.66): calc.: C, 56.34; H, 9.98; N, 4.87; P, 5.38. found: C, 56.01; H, 10.07; N, 4.98; P, 5.53.

N,N-bis-(2-chloroethyl)-amido-N'-(1-octadecyl-2-dodecyl-3-desoxy-sn-glycerol)-3-amidophosphoric acid methyl ester ($C_{38}H_{79}Cl_2N_d\,_2O_4$; 729.96): calc.: C, 62.53; H, 10.91; N, 3.84; P, 4.24. found: C, 62.68; H, 11.06; N, 4.03; P, 4.32.

(B) Amidolysis:
N,N-bis-(2-chloroethyl)-N'-alkyl-N''-phosphotriamide (Transport Form)

The solution in THF (B; 0.1 mol) is mixed with excess amine (1 mol). After ending of the reaction (TLC verification), it is mixed with 200 ml. chloroform and washed twice with 200 ml. water. The solvent is stripped off and the residue chromatographed on silica gel. The yields lie at 90%.

The following compounds were prepared in this way:

N,N-bis-(2-chloroethyl)-N'-(1-octadecyl-2-methyl-3-desoxy-sn-glycerol)-phosphporic acid triamide ($C_{26}H_{56}Cl_2N_3O_3P$; 560.65): calc.: C, 55.70; H, 10.07; N, 7.50; P, 5.53. found: C, 55.81; H, 10.14; N, 7.39; P, 5.24.

N,N-bis-(2-chloroethyl)-N'-(1-octadecyl-2-methyl-3-desoxy-sn-glycerol)-N''-methylphosphoric acid triamide ($C_{27}H_{58}Cl_2N_3O_3P$; 575.674): calc.: C, 56.43; H, 10.17; N, 7.31; P, 5.39. found: C, 56.65; H, 10.26; N, 7.24; P, 5.20.

N,N-bis-(2-chloroethyl)-N'-(1-octadecyl-2-methyl-3-desoxy-sn-glycerol)-N''-dimethylphosphoric acid triamide ($C_{28}H_{60}Cl_2N_3O_3P$; 588.70): calc.: C. 57.13; H, 10.27; N, 7.14; P, 5.26. found: C, 57.24; H, 10.35; N, 6.911 P, 5.01.

N,N-bis-(2-chloroethyl)-N'-(1-octadecyl-2-methyl-3-desoxy-sn-glycerol)-N''-diethylphosphoric acid triamide calc.: C, 57.13; H, 10.27; N, 7.14; P, 5.26. found: C, 57.09; H, 10.41; N, 7.22; P, 5.14.

I claim:

1. A derivative of N,N-bis-(2-chloroethyl)-phosphoric acid amide of the formula I

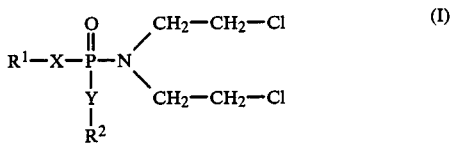

wherein
X is O;
Y is O or $NR^3$; $R^1$ is $CH_2(OR^4)—CH(OR^5)—CH_2—$, $R^2$ is hydrogen, methyl, ethyl or propyl and when Y is $NR^3$, $R^2$ can also be hydrogen; and when $R^2$ is not hydrogen, Y may only be O; $R^3$ is hydrogen, methyl, ethyl or propyl; $R^4$ and $R^5$ are the same or different and represent an alkyl radical R or an acyl radical —COR, wherein the alkyl or acyl moiety R is a straight-chained or branched, saturated or unsaturated alkyl group with 1 to 25 carbon atoms, or an aralkyl radical with 1 to 25 carbon atoms in the alkyl chain, and one of the radicals can also be a hydrogen atom, with the proviso that at least one of the residues $R^4$ or $R^5$ is an alkyl radical of 16 to 20 carbon atoms or an acyl radical having an alkyl moiety of 16 to 20 carbon atoms.

2. Compounds according to claim 1 characterized in that $R^2$ is methyl.

3. A derivative of N,N-bis-(2-chloroethyl)-phosphoric acid amide of the formula I:

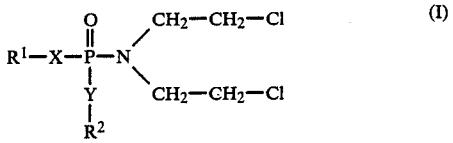

wherein
$R^1$ is 3-octadecyloxy-2-methoxypropyl,
$R^2$ is methyl, X is NH and
Y is oxygen.

4. Medicaments containing an antitumor effective amount of the compound of the formula I according to claim 1 in a pharmaceutically acceptable carrier.

* * * * *

UNITED STATES PATENT AND TRADEMARK OFFICE
CERTIFICATE OF CORRECTION

PATENT NO. : 4,739,095

DATED : April 19, 1988

INVENTOR(S) : Eibl

It is certified that error appears in the above-identified patent and that said Letters Patent is hereby corrected as shown below:

Col. 4, line 13: delete "-CH(CH$_2$)-CH$_2$-" and insert -- -CH(CH$_3$)-CH$_2$- --.

Col. 5, line 32: delete "(C$_{38}$H$_{79}$Cl$_2$N$_{d2}$O$_4$;" and insert -- (C$_{38}$H$_{79}$Cl$_2$N$_2$O$_4$; --.

Col. 5, line 48: after "-glycerol)-" delete "phosphporic" and insert -- phosphoric --.

Col. 6, line 5: after "N" delete "6.911" and insert -- 6.91 --.

Signed and Sealed this

Fourteenth Day of March, 1989

Attest:

DONALD J. QUIGG

Attesting Officer

Commissioner of Patents and Trademarks